United States Patent [19]

Brown et al.

[11] Patent Number: 5,157,204
[45] Date of Patent: Oct. 20, 1992

[54] REMOVAL OF IMPURITIES FROM HYDROCARBON FEEDS

[75] Inventors: Scott H. Brown, Bartlesville, Okla.; John H. Kolts, Idaho Falls, Id.

[73] Assignee: Phillips Petroleum Company, Bartlesville, Okla.

[21] Appl. No.: 715,943

[22] Filed: Jun. 14, 1991

[51] Int. Cl.$^5$ .......... C07C 7/152; C07C 7/00; C01B 31/18

[52] U.S. Cl. .................. 585/850; 585/852; 585/855; 423/247; 423/246

[58] Field of Search .......... 585/850, 852, 855; 423/247, 246

[56] References Cited

U.S. PATENT DOCUMENTS

| | | | |
|---|---|---|---|
| 2,837,587 | 6/1958 | Hogan et al. | 260/683.15 |
| 2,980,743 | 4/1961 | Toft | 260/677 |
| 3,549,719 | 12/1970 | Duyverman et al. | 260/677 |
| 3,907,964 | 9/1975 | Whitman et al. | 423/213.2 |
| 4,185,039 | 1/1980 | Eden | 260/654 A |
| 4,582,950 | 4/1986 | Busse et al. | 585/833 |
| 4,818,745 | 4/1989 | Kolts | 502/327 |
| 4,830,844 | 5/1989 | Kolts | 423/437 |
| 4,902,660 | 2/1990 | Delzer et al. | 502/174 |
| 4,920,088 | 4/1990 | Kolts | 502/326 |
| 4,921,830 | 5/1990 | Kolts | 502/326 |
| 4,940,686 | 7/1990 | Tooley et al. | 502/327 |
| 4,943,550 | 7/1990 | Kolts et al. | 502/327 |
| 4,956,330 | 9/1990 | Elliott et al. | 502/326 |

*Primary Examiner*—Anthony McFarlane
*Assistant Examiner*—Nhat Phan
*Attorney, Agent, or Firm*—K. K. Brandes

[57] ABSTRACT

A process for removing carbon monoxide and free oxygen from hydrocarbon-containing fluids comprises contacting the fluid feed with at least one of several supported platinum-containing catalyst compositions so as to convert carbon monoxide and free oxygen to carbon dioxide, essentially without oxidizing the hydrocarbon(s).

20 Claims, No Drawings

REMOVAL OF IMPURITIES FROM HYDROCARBON FEEDS

BACKGROUND OF THE INVENTION

This invention relates to the removal of CO and $O_2$ contained in hydrocarbon feeds by catalytic oxidation to $CO_2$. In a particular aspect, this invention relates to the removal of CO and $O_2$ contained in monoolefin-containing streams.

The presence of carbon monoxide impurities, and also of molecular oxygen, in hydrocarbon containing fluids is undesirable for a variety of reasons. This is particularly true for monoolefin-containing feeds for catalytic polymerization processes, such as the polymerization of ethylene and/or propylene in the presence of Ziegler-Natta catalysts, because CO and $O_2$ poison these catalysts. Even though it is known to remove CO and $O_2$ from hydrocarbon-containing feeds by catalytic oxidation, the known cleanup processes generally operate at elevated temperatures and at a stoichiometric excess of free oxygen. Under these oxidation conditions, not only CO but also a portion of the hydrocarbons will generally be oxidized. The present invention provides a process which alleviates the undesirable oxidation of hydrocarbons during the catalytic oxidation of CO with $O_2$.

SUMMARY OF THE INVENTION

It is an object of this invention to remove carbon monoxide and free oxygen present in hydrocarbon-containing fluids by catalytic oxidation to carbon dioxide. It is another object of this invention to remove CO and $O_2$ from monoolefin-containing feeds. It is a further object of this invention to provide a process for catalytically converting CO and $O_2$ present in hydrocarbon-containing fluids to $CO_2$ under such conditions that substantially no hydrocarbons are oxidized. Other objects and advantages will become apparent from the detailed description of this invention and the appended claims.

In accordance with this invention, a process for removing carbon monoxide and free oxygen from hydrocarbon-containing fluids comprises contacting (a) a fluid feed which comprises at least one hydrocarbon containing up to 10 carbon atoms per molecule, carbon monoxide and free oxygen with (b) at least one platinum-containing catalyst composition, at such contacting conditions as to obtain a fluid product which contains less carbon monoxide and free oxygen than the feed and contains essentially the same amount of the hydrocarbon as the feed; wherein said at least one platinum-containing catalyst composition is selected from the group consisting of (1) catalyst compositions comprising platinum metal, iron oxide, and at least one inorganic support material selected from the group consisting of alumina, alumina-coated porous ceramic monolith, magnesia, magnesia-coated porous ceramic monolith, magnesium aluminate, magnesium aluminate-coated porous ceramic monolith, hydrotalcite, titania, titania-coated porous ceramic monolith, zirconia, zirconia-coated porous ceramic monolith, and vanadia; and (2) catalyst compositions comprising platinum metal, palladium metal, at least one manganese compound, optionally at least one chromium compound, and a tin dioxide-coated porous ceramic monolith as support material.

DETAILED DESCRIPTION OF THE INVENTION

Any suitable hydrocarbon-containing fluid which also contains carbon monoxide and free oxygen can be employed as a feed in the process of this invention. The feed hydrocarbon(s) contain up to 10, preferably about 1 to 10, carbon atoms per molecule. The feed fluid can be liquid or gaseous, preferably gaseous. Non-limiting examples of hydrocarbons contained in the feed include linear and branched paraffins (alkanes), preferably containing 1-10 carbon atoms per molecule (more preferably methane, ethane, propane, n-butane, isobutane, n-pentane and isopentanes), linear and branched monoolefins (alkenes), preferably containing 2-10 carbon atoms per molecule (more preferably ethylene, propylene, butene-1, butene-2, isobutylene, pentene-1, pentene-2, 2-methylbutene-1 and 2-methylbutene-2; in particular ethylene and/or propylene); diolefins (alkadienes), preferably containing 4-10 carbon atoms per molecule (more preferably 1,2-butadiene, 1,4-butadiene, isoprene, 1,2-pentadiene and 1,4-pentadiene); acetylenes (alkynes), preferably containing 2-10 carbon atoms (more preferably ethyne and propyne); cycloalkanes, preferably containing 5-10 carbon atoms per molecule (more preferably cyclopentane, cyclohexane, cycloheptane and methylcyclohexane); cycloalkenes, preferably containing 5-10 carbon atoms per molecule (more preferably cyclopentene, cyclohexene, cycloheptene and methylcyclohexene); cycloalkadienes, preferably containing 5-10 carbon atoms per molecule (more preferably 1,3-cyclopentadiene, 1,3-cyclohexadiene and 1,4-cyclohexadiene); and aromatic hydrocarbon, preferably containing 6-10 carbon atoms per molecule (more preferably benzene, toluene, o-, m- and p-xylenes, 1,3,5-trimethylbenzene, ethylbenzene, 1-methyl-2-ethylbenzene). Presently most preferred are monoolefin-containing feeds, in particular ethylene- and propylene-containing feeds.

Generally, the feed can contain from about 90 to about 99.999 (preferably about 98-99.9) mole percent of at least one hydrocarbon (i.e., one or two or more than two hydrocarbons which may be from the same or from different hydrocarbon series). The feed contains carbon monoxide (as an impurity), generally at a level of about 0.1 mole-ppm CO (moles of CO per million moles of the feed) to about 6 mole-percent CO, more particularly at a level of about 1 mole-ppm CO to about 0.4 mole-percent CO. Free oxygen is also present in the feed. Generally, the content of free oxygen in the feed is in the range of about 0.05 mole-ppm $O_2$ (moles of $O_2$ per million moles of the feed) to about 3 mole-percent $O_2$, preferably about 0.5 mole-ppm $O_2$ to about 0.2 mole percent $O_2$. Any suitable molar ratio of $O_2$:CO can be employed. Preferably the molar ratio of $O_2$ to CO is about 0.5:1 (i.e., essentially stoichiometric).

It is within the scope of this invention to employ feeds which originally contained very little or essentially no free oxygen. In this case, a suitable amount of a free oxygen-containing gas (such as essentially pure $O_2$ or air or $O_2$-enriched air) is mixed with the hydrocarbon-containing feed so as to attain a desired molar ratio of $O_2$:CO, preferably about 0.5:1. Other impurities (besides CO and $O_2$), such as $N_2$, $CO_2$, $H_2S$, mercaptans, arsines, mercury compounds, may be present in the feed, as long as they do not adversely affect the process of this invention (e.g., by poisoning the CO oxidation catalyst).

The catalysts which are employed in the CO removal process of this invention are known and have been described in numerous patents. U.S. Pat. No. 4,830,844 discloses catalysts comprising (preferably consisting essentially of) Pt, Pd, Mn compound(s) on a $SnO_2$-coated ceramic monolith; Pt, Pd, Cr compound(s) on $SnO_2$-coated ceramic monolith; and Pt, Pd, Mn and Cr compound(s) on $SnO_2$-coated ceramic monolith. Cordierite is a preferred porous ceramic monolith. Any suitable promoter levels in these catalysts can be employed. Preferably, the promoter levels, based on the weight of the catalyst excluding the monolith, are in the range of about 0.5–10 weight-% (Pt+Pd), about 0.1–4 weight-% Mn and/or about 0.1–4 weight-% Cr.

U.S. Pat. Nos. 4,818,745 and 4,943,550 disclose catalysts comprising (preferably consisting essentially of) Pt and Fe-oxide on alumina; Pt and Fe-oxide on magnesia; and Pt and Fe-oxide on magnesium aluminate. Any suitable promoter levels in these catalysts can be chosen. Preferably, the promoter levels are about 0.5–5 weight-% Pt and about 0.1–4 weight-% Fe. Pd can also be present as a promoter, preferably, at a level of about 1–3 weight-% Pd. It is also possible to have the alumina or magnesia or Mg-aluminate support materials coated upon a ceramic monolith material (preferably cordierite), as is described in the above-mentioned patents. When a ceramic monolith is present in the above-described catalysts, the above-recited weight percentages of Pt, Fe and Pd are based on the total weight of the catalyst (including the monolith).

U.S. Pat. No. 4,902,660 discloses catalysts comprising (preferably consisting essentially of) Pt and Fe-oxide on hydrotalcite, preferably having been prepared by a method comprising impregnation of hydrotalcite with a solution containing Pt and Fe compounds and having a pH of at least about 5. Any suitable promoter levels in these catalysts can be employed. Preferably, these promoter levels are about 0.5–5 weight-% Pt and about 0.1–4 weight-% Fe. Optionally, Pd can also be present as promoter, preferably at a level of about 1–3 weight-% Pd.

U.S. Pat. Nos. 4,920,088 and 4,921,830 disclose catalysts comprising (preferably consisting essentially of) Pt and Fe-oxide on $TiO_2$ or $ZrO_2$. Any suitable promoter levels in these catalysts can be employed, preferably these levels are about 0.5–5 weight-% Pt and about 0.1–4 weight-% Fe. Other copromoters can also be present, such as palladium (preferably about 1–3 weight-% Pd) and silver (preferably about 0.2–4 weight-% Ag). Furthermore, $TiO_2$ or $ZrO_2$ can be applied as coating on a ceramic monolith (preferably cordierite) support material, as is described in the above-cited patents. In the case of the Pt/Fe-oxide/$TiO_2$ catalyst, at least one alkali metal compound (preferably a potassium compound) can also be present as a copromoter, preferably at a level of about 0.1–5 weight-% alkali metal, as is described in U.S. Pat. No. 4,956,330. When a ceramic monolith is present in the catalyst, the above-recited weight percentages of Pt, Fe, Pd, Ag and alkali metal are based on the weight of the catalyst excluding the monolith.

U.S. Pat. No. 4,940,686 discloses catalysts comprising (preferably consisting essentially of) Pt and Fe-oxide on vanadium oxide. Preferably, the vanadium oxide is $V_2O_5$. Any suitable promoter levels in the catalyst can be employed. Preferably, the promoter levels are about 0.2–10 weight-% Pt (more preferably about 0.5–5 weight-% Pt) and about 0.1–20 weight-% Fe (more preferably about 0.1–4 weight-% Fe). Optionally, alumina can also be present in the catalyst support component (besides V-oxide), generally at a weight ratio of alumina to vanadium oxide in the range of about 30:1 to about 1:1, as is described in the above-cited patent.

Any suitable process conditions can be employed in the process of this invention. Generally, the process is conducted continuously, wherein a fluid feed stream which contains hydrocarbon(s), carbon monoxide and free oxygen is introduced into a reactor which contains one or two or more than two of the catalyst compositions described above. The catalyst composition(s) can be present in any suitable arrangement, i.e., in a fluidized catalyst bed, or in a moving catalyst bed, or (preferably) in a fixed catalyst bed. The contacting temperature (i.e., the average temperature of feed and catalyst composition(s) in the contacting zone (such as a fixed bed) generally is in the range of about $-30°$ C. to about $200°$ C., preferably about $-25°$ C. to about $100°$ C., more preferably about $0°-30°$ C. The total pressure during the contacting generally is about 1 to about 150 atm (about 15–2180 psia). If the feed is liquid, the liquid hourly space velocity of the feed (LHSV expressed as volume feed per volume catalyst per hour) is in the range of about 0.1 to about 20 (preferably about 0.5–5). If the feed is gaseous, the gas hourly space velocity of the feed (GHSV, expressed as volume feed per volume catalyst per hour) is in the range of about 100 to about 50,000 (preferably about 1,000–10,000).

The product of the process of this invention contains essentially the entire amount of hydrocarbon(s) which has been present in the feed. The product also contains $CO_2$ (produced by the reaction of CO and $O_2$) and possibly other impurities (such as $N_2$ if air has been added to the feed, unconverted $O_2$, and unconverted CO). The product can be further purified, if desired, in any suitable manner, such as by distillation, adsorption (e.g., by molecular sieves), membrane separation and the like, mainly for removing $CO_2$ and possibly other impurities from the hydrocarbon-containing product.

The following examples are presented in further illustration of the invention and are not to be considered as unduly limiting the scope of this invention.

EXAMPLE I

This example illustrates the removal of CO from a monoolefin feed by oxidation with $O_2$, in accordance with a known process and in accordance with a process within the scope of this invention. Three catalysts were tested:

Catalyst A (Control) was a catalyst containing 0.5 weight-% rhodium on ⅛" alumina pellets. This catalyst was provided by Strem Chemicals, Inc. Newburyport, Mass., and is representative of the catalyst used in the known CO removal process of U.S. Pat. No. 2,980,743.

Catalyst B1 was a catalyst containing 2.0 weight-% Pt, 0.8 weight-% Fe (as iron oxide) on ⅛" alumina pellets, prepared substantially in accordance with the procedure of U.S. Pat. No. 4,943,550. S-100 alumina pellets (provided by Aluminum Company of America, Pittsburgh, Pa.), which had previously been calcined for 16 hours in air at $800°$ C., were agitated with a sonic mixing device for 2 minutes while suspended in water. The supernatant aqueous phase containing suspended small alumina particles and impurities was separated from the alumina pellets, which were then rinsed with water.

This procedure was repeated twice, followed by drying at 140° C. and calcining for 2 hours in air at 400° C. 30 grams of the thus-treated alumina pellets were impregnated with a solution of 1.21 grams Pt(II) acetylacetonate and 1.52 gram Fe(III) acetylacetonate in 50 cc acetone. The thus-impregnated alumina pellets were dried, calcined for 3 hours in air at 400° C., heated for 2 hours in hydrogen gas at 300° C., cooled to room temperature in a nitrogen purge gas stream, wetted with concentrated nitric acid, calcined for 3 hours in air at 400° C., sonically agitated twice while suspended in distilled water (as described above), dried, calcined for 3 hours in air at 400° C., and heated for 2 hours in hydrogen gas at 300° C.

Catalyst B2 was the same as Catalyst B1 except that it contained 0.5 weight-% Pt and 0.2 weight-% Fe (as iron oxide).

The above-described catalysts were tested as follows: A gaseous feed containing 98.4 volume-% ethylene, 1.0 volume-% $N_2$, 0.4 volume-% CO and 0.2 volume-% $O_2$ was introduced at a feed rate of 100 cc/minute into a quartz reactor having an inner diameter of 7 mm and containing 2.0 grams of Catalyst A or B1 or B2. For low temperature tests, the quartz reactor was placed inside a Thermotron S-4C environmental chamber, which could be cooled to as low as −73° C. The gas feed was precooled by passing it through a 3 foot long coiled stainless steel tube placed in the environmental chamber. When the tests were carried out at elevated temperatures, the environmental chamber was replaced with a furnace, and the gas feed was not preheated. All feed gas samples and product gas samples were analyzed by means of a Model 102 Applied Automation Gas Chromatograph. Test results are summarized in Table I.

TABLE I

| Reaction Temp. (°C.) | Catalyst | Time on Stream (Hr.) | % Conversion of CO |
|---|---|---|---|
| −25° C. | B1 | 1 | 55 |
| | | 2 | 47 |
| | | 4 | 35 |
| 0° C. | A (Control) | 1 | 0 |
| | | 2 | 0 |
| 0° C. | B1 | 1 | 81 |
| | | 2 | 75 |
| 25° C. | A (Control) | 1 | 4 |
| | | 2 | 1 |
| 25° C. | B1 | 1 | 97 |
| | | 2 | 95 |
| 25° C. | B2 | 1 | 41 |
| | | 2 | 20 |
| 100° C. | A (Control) | 1 | 27 |
| | | 2 | 21 |
| 100° C. | B1 | 1 | 98 |
| | | 2 | 97 |
| | | 4 | 100 |

Note: No oxidation of ethylene was detected in any of the above test runs.

The above test results clearly indicate that the Pt/Fe-oxide/$Al_2O_3$ catalysts (Pt content: 0.5–2 weight-%) were considerably more effective as catalysts for removing CO from a monoolefin feedstream than Rh/$Al_2O_3$ (Rh content: 0.5 weight-%).

A catalyst which was substantially the same as Catalyst B1 was employed in a separate CO oxidation test for about 20 hours at about 25° C., essentially in accordance with the above-described test procedure. Attained CO conversions were 96% after 5 hours on stream, 74% after 10 hours on stream, and 59% after 20 hours on stream.

Two commercial Pt/$Al_2O_3$ automobile exhaust catalysts were also tested at about 25° C. for CO removal from ethylene streams, essentially in accordance with the test procedure described above. These commercial catalyst exhibited no or very low CO conversions, ranging from 0% to 2% after 1 hour on stream at about 25° C.

EXAMPLE II

This example also illustrates the removal of CO from hydrocarbon-containing gases by oxidation with $O_2$ in the presence of supported Pt/Fe-oxide catalysts (within the scope of the present invention).

Catalyst C was a Pt/Fe-oxide/$TiO_2$ catalyst containing 3.5 weight-% Pt and 1.5 weight-% Fe (as iron oxide) on 3/16" $TiO_2$ pellets. This catalyst was prepared substantially in accordance with the procedure described in U.S. Pat. No. 4,920,088, by impregnation of $TiO_2$ with an aqueous solution of $Pt(NH_3)_4(NO_3)_2$ and $Fe(NO_3)_3$, followed by drying at 125° C., calcining for 3 hours in air at 400° C., and heating in $H_2$ for 2–3 hours at 300° C.

Catalyst D was a Pt/Fe-oxide/$MgAl_2O_4$ catalyst containing 3.5 weight-% Pt and 1.5 weight-% Fe on $MgAl_2O_4$ tablets. This catalyst was prepared substantially in accordance with the procedure described in U.S. Pat. No. 4,943,550. $MgAl_2O_4$ tablets (5.1×5.4 mm; supplied by Haldor-Topsoe, Inc., Houston, Tex., under the product designation CAM-9L) were repeatedly sonically agitated while suspended in distilled water (as described for Catalyst B1), rinsed, dried at 140° C., calcined for 2 hours in air at 400° C., and allowed to cool to room temperature. The thus-treated $MgAl_2O_4$ tablets were repeatedly impregnated with an aqueous solution of $Pt(NH_3)_4(NO_3)_2$ and $Fe(NO_3)_3$, dried at 140° C. and calcined for 2 hours in air at 400° C. The thus-impregnated tablets were heated for 2 hours in $H_2$ at 300° C., allowed to cool to room temperature in a $N_2$ purge gas stream, wetted with concentrated nitric acid, dried at 140° C., calcined for 2 hours in air at 400° C., sonically agitated while suspended in distilled water (as described for Catalyst B1), rinsed with water, dried at 140° C., calcined for 2 hours in air at 400° C., and heated for 2 hours in hydrogen gas at 300° C.

Catalysts C and D were tested for CO removal from monoolefin-containing feeds at 25°–30° C. substantially in accordance with the procedure described in Example I, using either an ethylene feed gas or a propane/propylene feed gas. The feed propane/propylene-containing gas, when used, contained 50.7 volume-% propane, 47.7 volume-% propylene, 1 volume-% $N_2$, 0.4 volume-% CO and 0.2 volume-% $O_2$. The ethylene containing feed gas, when used, had approximately the same composition as the feed gas described in Example I. Test results (obtained at a reaction temperature of 25°–30° C.) are summarized in Table I.

TABLE II

| Feed Gas | Catalyst | Time on Stream (Hr.) | % Conversion of CO |
|---|---|---|---|
| Ethylene | C | 1 | 98 |
| | | 2 | 90 |
| | | 4 | 73 |
| | | 6 | 62 |
| Ethylene | D | 1 | 93 |
| | | 2 | 89 |
| | | 4 | 82 |
| | | 5 | 80 |
| Propane/Propylene | D | 1 | 69 |
| | | 2 | 66 |
| | | 4 | 55 |
| | | 6 | 55 |

TABLE II-continued

| Feed Gas | Catalyst | Time on Stream (Hr.) | % Conversion of CO |
|---|---|---|---|
| Propane/Propylene | D[1] | 1 | 95 |
| | | 2 | 87 |
| | | 4 | 84 |
| | | 6 | 76 |
| | | 10 | 68 |
| | | 20 | 53 |

Note: Catalyst D[1] was a regenerated Catalyst D, wherein Catalyst D was heated at 400° C. in air, purged with $N_2$ at 300° C. and then heated in $H_2$ for 2 hours at 300° C.

Test data in Table II clearly demonstrate the effectiveness of the two above-described Pt/Fe-oxide catalysts (within the scope of this invention) for CO removal from alkenes and/or alkanes.

EXAMPLE III

This example illustrates the use of two platinum catalysts containing coated monolith supports for removal of CO from monoolefin-containing feeds (within the scope of the present invention).

Catalyst E was a Pt/Fe-oxide catalyst on a $MgAl_2O_4$-coated ceramic monolith support containing 1.0 weight-% Pt, 0.5 weight-% Fe, 5.1 weight-% $MgAl_2O_4$ coating, and a cordierite monolith ceramic support material (2 $MgO.2Al_2O_3.5SiO_2$; available from Corning Glass Works, Corning, N.Y.) as the remainder. This catalyst was prepared as follows: A cylindrical cordierite monolith (having 100 cells/inch$^2$, 1 inch diameter and 1 inch height) was repeatedly dipped into an aqueous solution containing 27.1 grams $Mg(NO_3)_2.6H_2O$ and 79.1 grams $Al(NO_3)_3.9H_2O$ in 200 cc distilled water. After each dipping, the monolith was dried at 200° C. After about 10 dipping/drying cycles, the coated monolith was calcined for 10 hours in air at 700° C. so as to obtain a coating of about 5 weight-% $MgAl_2O_4$ on the monolith. The $MgAl_2O_4$-coated monolith was then impregnated several times with a solution of 0.116 g Pt(II) acetylacetonate and 0.182 g Fe(II) acetylacetonate in 20 cc acetone, followed by drying, calcining for 3 hours in air at 400° C., heating for 2 hours in hydrogen gas, wetting with concentrated nitric acid, recalcining at 400° C. in air, and rereducing for 2 hours in $H_2$ and 400° C.

Catalyst F1 was a Pt/Pd/Mn catalyst on a $SnO_2$-coated ceramic monolith support containing 2.5 weight-% Pt, 2.5 weight-% Pd and 0.7 weight-% Mn, based on the weight of the catalyst excluding the weight of the monolith. This catalyst was prepared substantially in accordance with the procedure described in U.S. Pat. No. 4,830,844. First, a colloidal solution of hydrated $SnO_2$ was prepared by slowly dissolving 200 grams tin metal in a mixture of 800 cc concentrated $HNO_3$ and 600 cc distilled water, at a temperature of up to 50° C. Thereafter, the obtained solution was decanted from settled solid residue, 1 liter of distilled water was added to the solution, the decanting step was repeated several times, and 293 g of an aqueous 20 weight-% tetraethylammonium hydroxide solution was added as a stabilizer to the colloidal tin dioxide solution. Thereafter, a cordierite monolith (described above) was dipped seven times into the above-identified colloidal tin dioxide solution, with a drying step of 200° C. carried out after each dipping step. Then the $SnO_2$-coated monolith was repeatedly impregnated with aqueous solutions of $Pt(NH_3)_4(NO_3)_2$, $Pd(NH_3)_4(NO_3)_2$ and $Mn(NO_3)_2$, with drying steps (at 125°-300° C.) steps between each impregnation step, followed by calcining for 2 hours in air at 300° C., and heating in $H_2$ for 1 hour at about 50° C.

Catalyst F2 was substantially the same as Catalyst F1, except that it contained only 0.5 weight-% Pt, 0.5 weight-% Pd and 0.15 weight-% Mn; based on the weight of the catalyst excluding the weight of the monolith.

Samples of about 5.8 grams of Catalyst E, F1 and F2 were tested for removal of CO from an ethylene feed gas, substantially in accordance with the procedure described in Example I. All tests were carried out about 25°-30° C. and a feed gas rate of about 100 cc/minute. Test results are summarized in Table III.

TABLE III

| Catalyst | Time on Stream (Hrs.) | % Conversion of CO |
|---|---|---|
| E | 1 | 63 |
| | 2 | 48 |
| | 4 | 28 |
| | 6 | 28 |
| F1 | 1 | 98 |
| | 2 | 98 |
| | 4 | 97 |
| | 6 | 98 |
| | 10 | 100 |
| | 14 | 98 |
| F2 | 1 | 53 |
| | 2 | 35 |
| | 4 | 25 |
| | 6 | 24 |

Test date in Table III clearly show that the monolith-supported catalysts described in this example were quite effective for oxidizing CO contained in ethylene at room temperature, in accordance with the claimed process of this invention. A proprietary, commercial monolith-supported automobile exhaust catalyst exhibited CO conversion of only 3% at 25° C. after 1 hour on stream at the above-described testing conditions.

Reasonable variations and modifications are possible within the scope of the disclosure of this invention and the appended claims.

That which is claimed is:

1. A process for removing carbon monoxide and free oxygen from hydrocarbon-containing fluids which comprises contacting (a) a fluid feed consisting essentially of about 0.1 mole-ppm to about 6 mole-percent carbon monoxide, about 0.05 mole-ppm to about 3 mole-percent free oxygen, and at least one hydrocarbon containing up to 10 carbon atoms per molecule as the remainder of said feed with (b) at least one platinum-containing catalyst composition, at a reaction temperature in the range of about −30° C. to about 200° C. under such contacting conditions as to obtain a fluid product which contains less carbon monoxide and less free oxygen than said feed and contains essentially the same amount of said at least one hydrocarbon as said feed; wherein said at least one platinum-containing catalyst composition is selected from the group consisting of (1) catalyst compositions consisting essentially of platinum metal, iron oxide, and at least one inorganic support material selected from the group consisting of alumina, alumina-coated porous ceramic monolith, magnesia, magnesia-coated porous ceramic monolith, magnesium aluminate, magnesium aluminate-coated porous ceramic monolith, hydrotalicite, titania, titania-coated porous ceramic monolith, zirconia, zirconia-coated porous ceramic monolith, and vanadia;

(2) catalyst compositions consisting essentially of platinum metal, palladium metal, at least one manganese compound, and a tin dioxide-coated porous ceramic monolith as support material; and (3) catalyst compositions consisting essentially of platinum metal, palladium metal, at least one manganese compound, at least one chromium compound, and a tin dioxide-coated porous ceramic material.

2. A process in accordance with claim 1, wherein said at least one platinum-containing catalyst composition comprises platinum metal, iron oxide, and at least one inorganic support material selected from the group consisting of alumina, magnesia, magnesium aluminate, hydrotalcite, titania, zirconia and vanadia.

3. A process in accordance with claim 2, wherein said at least one platinum-containing catalyst composition contains about 0.5-5 weight-% Pt and about 0.1-4 weight-% Fe.

4. A process in accordance with claim 3, wherein the inorganic support material in said catalyst composition is alumina.

5. A process in accordance with claim 3, wherein the inorganic support material in said catalyst composition is magnesium aluminate.

6. A process in accordance with claim 3, wherein the inorganic support material in said catalyst composition is titania.

7. A process in accordance with claim 1, wherein said at least one platinum-containing catalyst composition comprises platinum metal, iron oxide, and at least one inorganic support material selected from the group consisting of alumina-coated porous ceramic monolith, magnesia-coated porous ceramic monolith, magnesium aluminate-coated porous ceramic monolith, titania-coated porous ceramic monolith, and zirconia-coated porous ceramic monolith.

8. A process in accordance with claim 7, wherein the inorganic support material in said catalyst composition is magnesium aluminate-coated ceramic monolith.

9. A process in accordance with claim 8, wherein said at least one platinum-containing catalyst composition contains about 0.5-5 weight-% Pt and about 0.1-4 weight-% Fe, based on the total weight of said catalyst composition.

10. A process in accordance with claim 1, wherein said at least one platinum-containing catalyst composition comprises platinum metal, palladium metal, at least one manganese compound, and a tin dioxide-coated porous ceramic monolith as support material.

11. A process in accordance with claim 10, wherein said at least one platinum-containing catalyst composition contains about 0.5-10 weight-% (Pt+Pd) and about 0.1-4 weight-% Mn, based on the weight of said catalyst composition excluding said ceramic monolith.

12. A process in accordance with claim 10, wherein said at least one platinum-containing catalyst composition further comprises at least one chromium compound.

13. A process in accordance with claim 12, wherein said at least one platinum-containing catalyst composition contains about 0.5-10 weight-% (Pt+Pd), about 0.1-4 weight-% Mn and about 0.1-4 weight-% Cr, based on the weight of said catalyst composition excluding said ceramic monolith.

14. A process in accordance with claim 1, wherein said at least one hydrocarbon in said feed contains 1-10 carbon atoms per molecule.

15. A process in accordance with claim 14, wherein said at least one hydrocarbon in said feed is at least one monoolefin.

16. A process in accordance with claim 15, wherein said at least one monoolefin is selected from the group consisting of ethylene and propylene.

17. A process in accordance with claim 1, wherein said feed contains about 1 mole-ppm to about 0.4 mole-percent carbon monoxide and about 0.5 mole-ppm to about 0.2 mole-percent of free oxygen.

18. A process in accordance with claim 17, wherein the molar ratio of free oxygen to carbon monoxide in said feed is about 0.5:1.

19. A process in accordance with claim 1, wherein said reaction temperature is about −25° C. to about 100° C.

20. A process in accordance with claim 1, wherein said feed contains about 90 to about 99.999 mole-% of said at least one hydrocarbon.

* * * * *